(12) United States Patent
Damadian et al.

(10) Patent No.: US 10,976,387 B1
(45) Date of Patent: Apr. 13, 2021

(54) MOTION PICTURE MRI

(71) Applicants: Raymond V. Damadian, Woodbury, NY (US); Michael Boitano, Smithtown, NY (US); Robert Wolf, Medford, NY (US); Jevan Damadian, New York, NY (US); John F. Greenhalgh, Greenlawn, NY (US)

(72) Inventors: Raymond V. Damadian, Woodbury, NY (US); Michael Boitano, Smithtown, NY (US); Robert Wolf, Medford, NY (US); Jevan Damadian, New York, NY (US); John F. Greenhalgh, Greenlawn, NY (US)

(73) Assignee: Fonar Corporation, Melville, NY (US)

( * ) Notice: Subject to any disclaimer, the term of this patent is extended or adjusted under 35 U.S.C. 154(b) by 1361 days.

(21) Appl. No.: 14/273,740

(22) Filed: May 9, 2014

Related U.S. Application Data

(62) Division of application No. 12/493,633, filed on Jun. 29, 2009, now abandoned.

(Continued)

(51) Int. Cl.
*A61B 5/05* (2021.01)
*G01R 33/28* (2006.01)
(Continued)

(52) U.S. Cl.
CPC .......... *G01R 33/286* (2013.01); *A61B 5/0037* (2013.01); *A61B 5/055* (2013.01);
(Continued)

(58) Field of Classification Search
CPC ... A61B 2090/374; A61B 34/20; A61B 5/055; A61B 2090/363; A61B 2017/00084;
(Continued)

(56) References Cited

U.S. PATENT DOCUMENTS 6,266,453 B1 * 7/2001 Hibbard ................ G06T 3/0006
382/131
6,301,497 B1 * 10/2001 Neustadter ......... G01R 33/4833
128/920

(Continued)

OTHER PUBLICATIONS

DiMaio et al., "Dynamic MRI Scan Plane Control for Passive Tracking of Instruments and Devices", MICCA, Oct.-Nov., pp. 50-58.*

(Continued)

*Primary Examiner* — Christopher L Cook
(74) *Attorney, Agent, or Firm* — Lerner, David, Littenberg, Krumholz & Mentlik, LLP

(57) ABSTRACT

Methods, apparatus and systems magnetic resonance imaging. The system may acquire images associated with a target region the body part including the target region moves, using a series of imaging planes correlated with the motion. The images are then displayed in time order sequence to provide a motion picture. The system may also provide for imaging in multiple planes such as mutually-perpendicular planes with rapid and facile switching between these planes. The multi-plane views can be used, for example, to monitor insertion of an instrument into the patient.

10 Claims, 9 Drawing Sheets

Related U.S. Application Data

(60) Provisional application No. 61/133,250, filed on Jun. 27, 2008.

(51) Int. Cl.
*A61B 5/055* (2006.01)
*A61B 19/00* (2006.01)
*A61B 5/00* (2006.01)

(52) U.S. Cl.
CPC ............ *A61B 5/7425* (2013.01); *A61B 19/54* (2013.01); *A61B 2019/5454* (2013.01)

(58) Field of Classification Search
CPC ...... A61B 2090/378; A61B 2090/3954; A61B 10/0233; A61B 8/0841; A61B 8/587; A61B 90/11; A61B 90/14; A61B 17/155; A61B 17/1764; A61B 2017/00694
See application file for complete search history.

(56) References Cited

U.S. PATENT DOCUMENTS

| | | | | |
|---|---|---|---|---|
| 6,533,794 | B2 * | 3/2003 | Chakeres | A61B 90/10 600/429 |
| 8,082,019 | B2 * | 12/2011 | Zhang | A61B 5/055 324/307 |
| 8,948,845 | B2 * | 2/2015 | Glossop | A61B 8/0841 600/424 |
| 2009/0124895 | A1 * | 5/2009 | Roden | A61B 34/10 600/427 |

OTHER PUBLICATIONS

Declaration of Robert Wolf with Exhibits A-F.

\* cited by examiner

BLUE PLANE: x-z PLANE
(CORONAL)

PURPLE PLANE: z-y PLANE
(SAGITTAL)

MOTION PICTURE MRI
WITH DISK AUTO-TRACKING

FIG. 6

SPINE RANGE-OF-MOTION PROCEDURE

910    INSTRUCT THE PATIENT TO ASSUME A NEUTRAL SITTING POSITION.

916    LOAD THE APPROPRIATE RPM PROTOCOL (E.G., CERVICAL SPINE SAGITTAL RPM).

922    INSTRUCT THE PATIENT TO HOLD STILL.

928    CLICK ON THE "SCAN" BUTTON.

934    USING THE "IN-OUT" MENU ITEM, TRANSLATE THE SAGITTAL IMAGE PLANE UNTIL THE DESIRED MID-LINE CUT IS OBTAINED.

940    USING THE "V-AXIS ROTATION" OR "H-AXIS ROTATION" MENU ITEM, MODIFY THE SAGITTAL IMAGE PLANE UNTIL THE DESIRED OBLIQUE SAGGITAL PLANE IS OBTAINED. REPEAT STEPS 934 AND 940 AS NECESSARY TO OPTIMALLY VISUALIZE THE REGION OF INTEREST.

946    INSTRUCT THE PATIENT TO SLOWLY BUT CONTINUOUSLY FLEX AND EXTEND HIS SPINE THROUGH A FULL RANGE OF MOTION.

952    IF DESIRED, THE "EXAMS" MENU ITEM CAN BE USED TO SWITCH TO PULSE SEQUENCES PROVIDING HIGHER RESOLUTION OR DIFFERENT CONTRAST.

958    REPEAT STEPS 934 AND 940 AS NECESSARY DURING FLEXION AND EXTENSION TO MAINTAIN VISUALIZATION OF ANATOMIC FEATURES OF INTEREST (E.G., LATERAL CUTS THROUGH THE NEURAL FORAMINA).

964    UPON COMPLETION OF THE STUDY, USE THE "EXIT" MENU ITEM TO STOP THE RPM ACQUISITION AND DISPLAY THE IMAGES IN A MOTION PICTURE.

MOTION PICTURE MRI

CROSS-REFERENCE TO RELATED APPLICATIONS

This application is a divisional of U.S. patent application Ser. No. 14/493,633, filed Jun. 29, 2009, which application claims the benefit of the filing date of U.S. Provisional Patent Application No. 61/133,250 filed Jun. 27, 2008, the disclosures of which are hereby incorporated herein by reference.

BACKGROUND OF THE INVENTION

The present invention relates to magnetic resonance imaging techniques and apparatus and processes for performing such techniques.

MRI (magnetic resonance imaging) has been widely adopted in the medical arts. Magnetic resonance imaging provides great anatomical detail and can characterize and discriminate among different tissues, in ways not available using other imaging techniques. MRI images also tend to be more detailed and often have more contrast than other imaging modalities. Moreover, because MRI does not use X-rays or other ionizing radiation, it offers safety advantages over techniques such as conventional X-ray imaging, fluoroscopy and CAT imaging. Indeed, in recent years the popularity of MRI has grown to the point where it is the preferred form of imaging for many conditions. In fact, it is not uncommon to read or hear a sports report that discusses the results of an athlete's MRI scan.

In magnetic resonance imaging, a strong, uniform magnetic field is applied to the region of the patient or anatomical area of interest to be imaged. Radio frequency ("RF") energy is then applied to the region of interest of the patient by a transmitter and antenna. The RF energy excites atomic nuclei within the patient's tissues. The excited nuclei spin or precess at a rate dependent upon the magnetic field. As they spin, they emit faint RF signals, referred to herein as magnetic resonance signals. By applying small magnetic field gradients so that the magnitude of the magnetic field varies with location within the patient's body, the magnetic resonance phenomenon can be limited to only a particular region, plane or "slice" of the patient's body, so that all of the magnetic resonance signals come from that region or slice. Moreover, by applying additional magnetic field gradients, the frequency and phase of the magnetic resonance signals from different locations within the slice can be made to vary in a predictable manner depending upon the position within the slice. Stated another way, the magnetic resonance signals are "spatially encoded," so that it is possible to distinguish between signals from different parts of a particular region, plane or slice.

If this process is repeated numerous times to elicit signals using different gradients, it is possible to derive a set of information, e.g., a set of image data, which indicates one or more characteristics of magnetic resonance signals from particular locations within the patient's body. Because the characteristics of the magnetic resonance signals vary with the concentration of different chemical substances and other chemical characteristics of the tissues, different tissues provide different magnetic resonance signal characteristics. When a magnetic resonance signal image data set is displayed in a visual format, such as on a computer screen or printed image, the information forms a still image or picture of the structures within the patient's body, with different tissues having different intensities or colors.

Typically, a set of magnetic resonance image data is stored as a set of individual data elements. The data in each element represents one or more characteristics of magnetic resonance signals from a small volume element or "voxel." For example, the map can be stored as a three-dimensional array of data elements, the dimensions of the array corresponding to three-dimensional space. Data elements corresponding to a given plane in three-dimensional space can be selected for display in a two-dimensional picture such as a screen display or printed image. Each small area element on the surface of the picture, commonly referred to as a "pixel," is assigned an intensity or color value based on the numerical values of the data element for the corresponding voxel. In many MRI procedures, data is acquired from a two-dimensional "slice" or set of voxels in an imaging area within a given plane and displayed as a two-dimensional image as, for example, on a video screen or printed image.

MRI allows visualization of tissues which are difficult or impossible to depict using other techniques. Magnetic resonance imaging can show abnormal tissues in contrast to surrounding normal tissues. For example, as disclosed in U.S. Pat. No. 3,789,832 of Raymond V. Damadian, magnetic resonance signals from malignant tumors have a characteristic referred to as the spin-lattice relaxation time or "$T_1$" different from the $T_1$ of normal tissues. If a magnetic resonance image is taken so that the data in each data element depends at least in part on the $T_1$ of the tissue at the corresponding location, a picture showing malignant tumor tissue in contrast to normal tissue can be displayed.

MRI is also particularly useful in imaging the spine. MRI can depict the vertebrae in conjunction with related tissues such as the lamina, and discs, as well as nerves, muscles and other neighboring tissues.

In magnetic resonance angiography, the magnetic field gradients applied during imaging, and the characteristics of the magnetic resonance signals which are translated into the image, are selected according to principles known in the art so that the data in voxels within arteries differs from the data for voxels in other structures, so that the arteries can be depicted in contrasting color or density to surrounding tissues. For example, arterial blood has a significant velocity and the surrounding tissues are nearly stationary. A so-called "motion-sensitive" MRI technique can be used so that a characteristic of the magnetic resonance signals from each voxel depends on the velocity of matter within the voxel. Magnetic resonance angiography yields images directly analogous to those obtained by conventional angiography, without the need for X-ray exposure. In some cases, MRI angiography can be performed without injection of a contrast medium. Moreover, MRI angiography can provide three-dimensional imaging information, so that images from any desired perspective can be displayed.

Most commonly, pictures derived from MRI images are read by a physician who visually examines the picture to diagnose disease which may be present or to evaluate the progress of a known disease. Such evaluation may involve, for example, a mental comparison by the physician with pictures the physician has previously seen of normal and other diseased patients or pictures taken in the past of the same patient. This task requires careful examination and considerable professional judgment. Even with the capabilities achievable in MRI imaging, it is not always easy to spot disease states or changes in the patient's condition.

In addition, the existence of some conditions may actually depend on the position of the patient, e.g., upright or supine, or on the type of movement that the anatomy undergoes. For example, often times symptoms associated with spinal maladies only exhibit themselves when a patient is in an upright, e.g., standing or sitting, position. In this regard, MRI magnet structures developed by Fonar Corporation, the assignee of the present application, have provided considerable versatility in MRI by allowing upright imaging in an open environment. As disclosed for example in commonly assigned, U.S. Pat. No. 6,677,753 ("'753 patent") and U.S. Pat. No. 6,414,490 ("'490 patent"), the disclosures of which are incorporated by reference herein, a pivotable and tiltable patient support, such as a bed, can be located in a static horizontal magnetic field so as to allow imaging a patient in multiple positions. Those positions include, for example, upright, recumbent, flexion and extension, kneeling, Trendelenburg and reverse Trendelenburg. In addition, these magnets also allow a patient to be imaged while the anatomy is in motion thereby allowing kinematic studies of the human anatomy in weight bearing or gravity bearing positions. Displaying of the sequence of individual static images resulting from such kinematic studies in sequence, so that the change from image to image appears to the eye like a progressively changing image is referred to as cine (i.e., cinematic) MRI.

Cine MRI, however, has its shortcomings. For example, cine MRI do not typically provide much enhancement in terms of diagnosis. All of the images constituting a conventional cine MRI typically are taken in a single plane in the frame of reference of the MRI magnet. For example, a cine MRI may show the patient's anatomy in a single vertical plane as the patient moves. It would be desirable to provide enhanced methods of cine imaging.

MRI can also be used to guide operative procedures. For example, it has been proposed to show a representation of a medical or surgical instrument superimposed on an MRI image during a procedure so that the physician can monitor the position of the instrument within the patient's body. However, it may be difficult for the physician to visualize the position the instrument in three-dimensional space. It would be desirable to provide methods of MRI imaging which simplify visualization.

Each of FIGS. 3B, 3C, 3D, 3E, and 3F is a diagrammatic view of an MRI image.

Figure 3A:
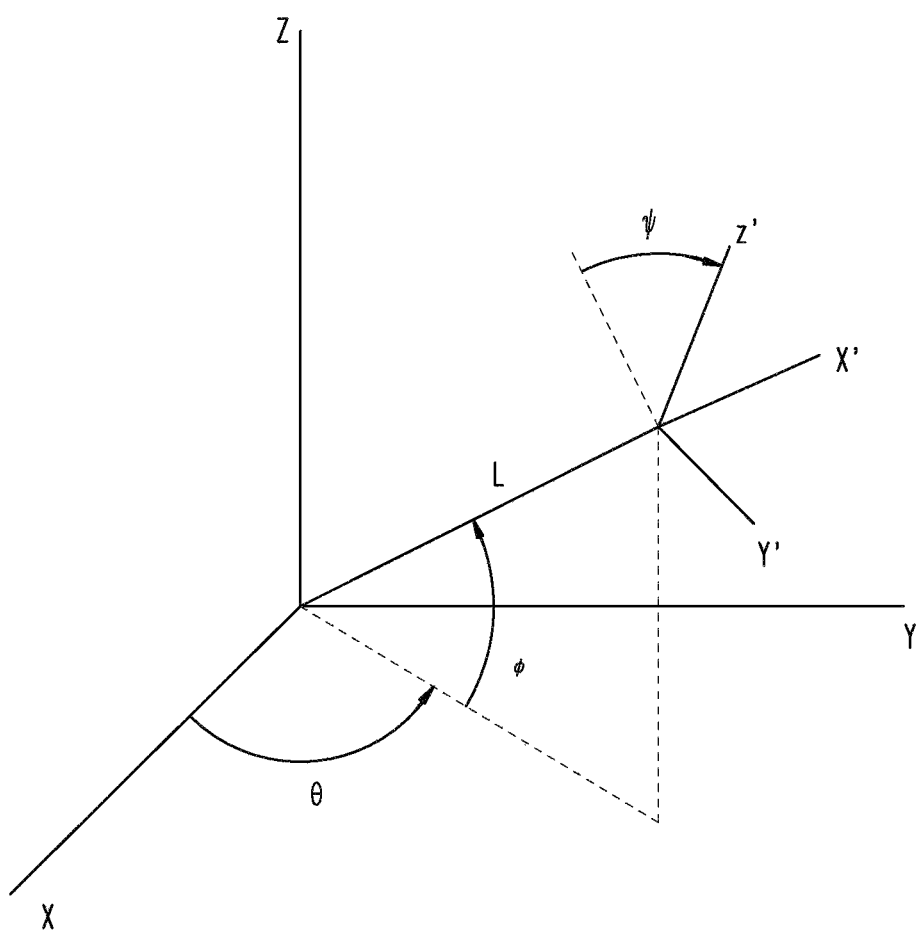
FIG. 3A depicts a reference coordinate system.
Figure 3B:
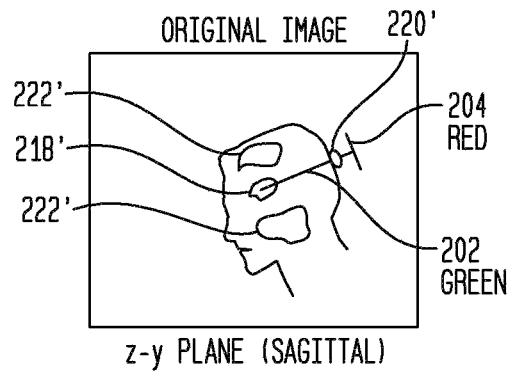
Figure 3C:
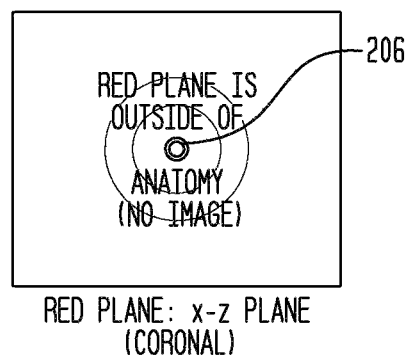
Figure 3D:
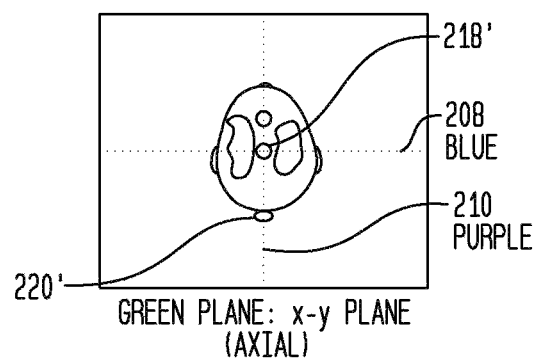
Figure 3E:
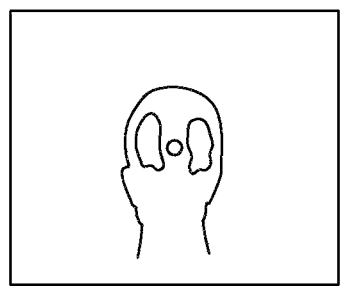
Figure 3F:
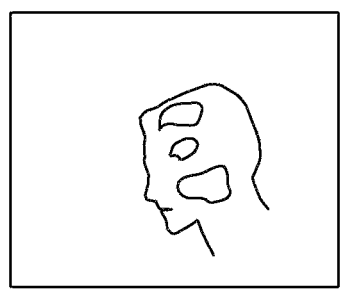
Figure 3G:
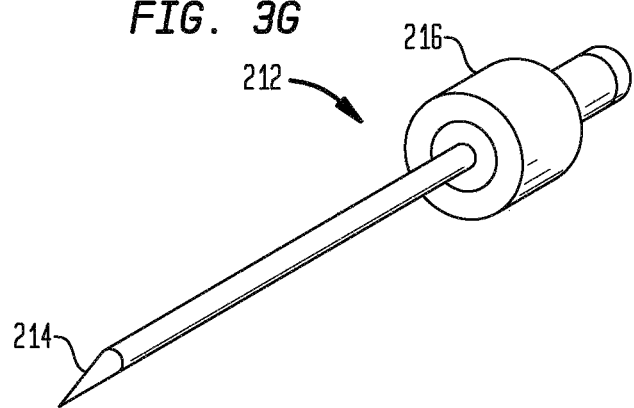

FIG. 3G is a diagrammatic perspective view of a medical instrument.

Figure 4A:
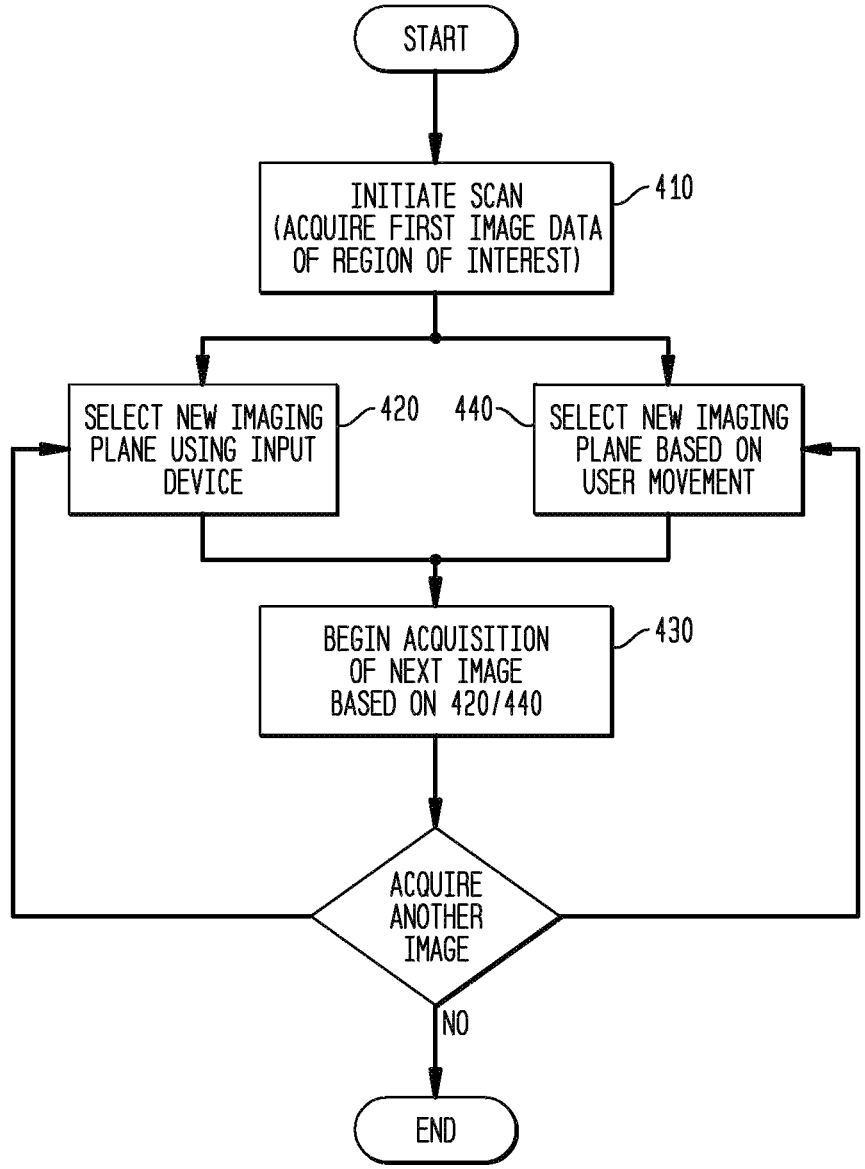
Figure 4B:
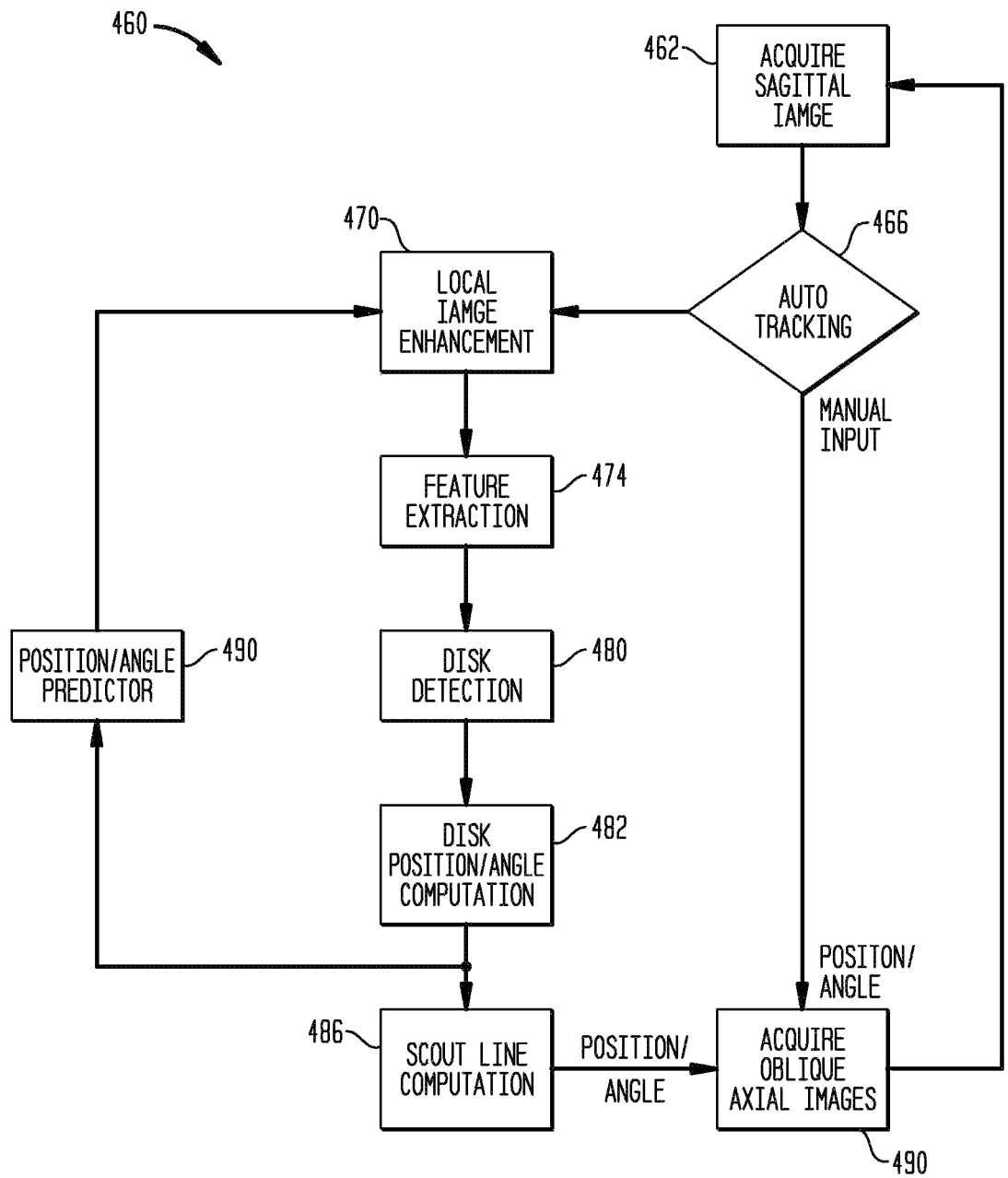

FIGS. 4A and 4B illustratively depict high level descriptions of methods or processes in accordance with aspects of the present invention.

Figure 5:
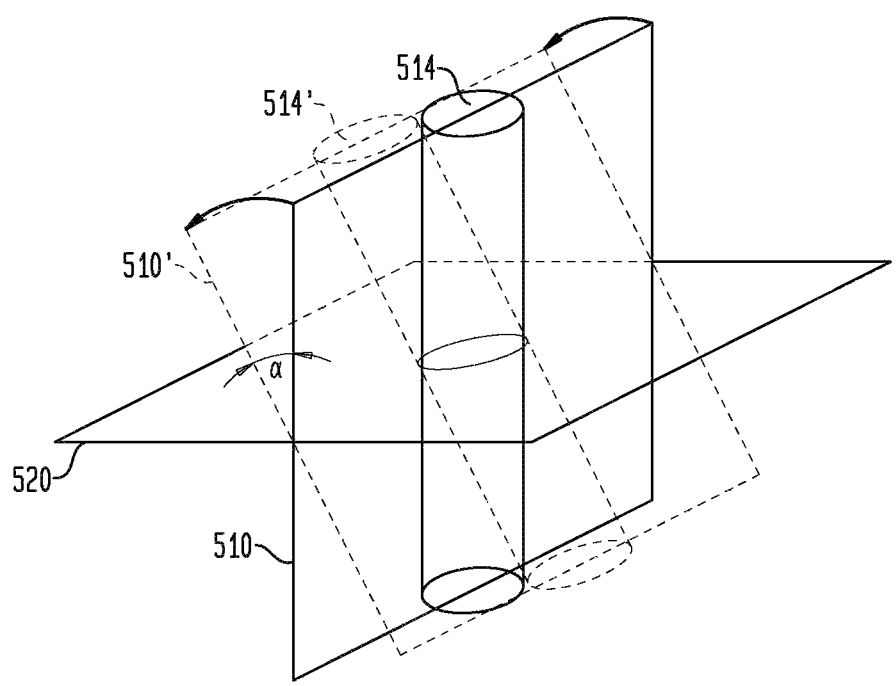

FIG. 5 illustratively depicts movement of an imaging plane and movement of a portion of a patient's anatomy.

FIG. 6 describes a method in accordance with one aspect of the present invention.

DETAILED DESCRIPTION

Figure 1:
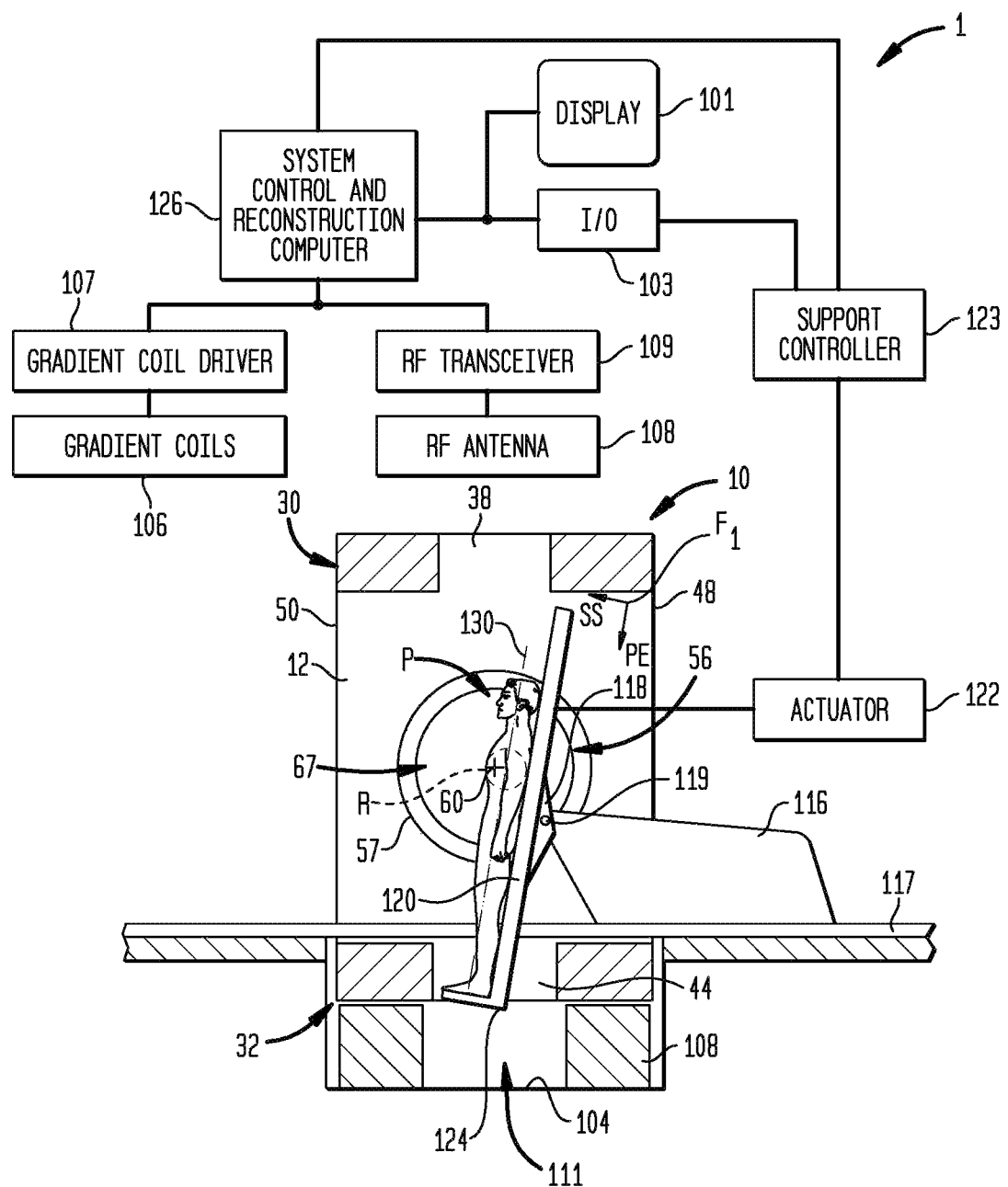
FIG. 1 is a sectional view of an apparatus used in accordance with an aspect of the present invention.

FIG. 1 depicts a sectional view of a magnetic resonance imaging system 1 that is used in accordance with an aspect of the present invention. Note, however, that the present invention is not limited by the particular system shown or by any preferred embodiment discussed herein. For example, the present invention's utility and advantages may be employed in a system such as that described in commonly assigned U.S. Patent Publication No. 2006-0197530-A1 (U.S. patent application Ser. No. 11/239,184), the disclosure of which is incorporated herein by reference. The system 1 according to one embodiment of the present invention includes a frame 10, which may comprise ferromagnetic material. As described in greater detail in the incorporated herein by reference '753 patent, the frame 10 is generally in the form of a hollow rectangular solid and includes a top flux return member 30 defining the top wall of the frame, a bottom flux return member 32 defining the bottom wall of the frame and a pair of generally vertical side walls 12 disposed opposite each other defining the sides of the frame, one such side wall 12 being visible in FIG. 1. The frame has patient entry openings 48 and 50 (FIG. 1) at front and back sides of the frame, i.e., the vertical sides which are not occupied by side wall 12 and an opposite side wall. The top flux return member 30 defines opening 38 in the top wall of the frame, whereas the bottom flux return member 32 defines an opening 44 in the bottom wall. The frame-like structure is maintained above a base structure 104 so that there is a space 111 beneath the bottom of the flux return member communicating with opening 44.

Two cylindrical poles 56 extend into the interior of the frame from the side walls 12. The poles extend on a common horizontal polar axis 60 and define a patient receiving space between them. The apparatus also includes a source of magnetic flux such as resistive or superconducting electromagnet coils 57 encircling the poles for providing a constant, substantially uniform static magnetic field within patient-receiving space 67.

A carriage 116 has a patient positioning assembly mounted thereon. The patient positioning assembly includes an elevator frame 118 pivotally mounted to the carriage for movement about a horizontal pivot axis 119. The patient positioning assembly further includes an elongated patient support or bed 120 with a footrest 124 at one end. The patient support is slidably mounted on the carriage. An actuator assembly 122 is provided for driving the carriage along rails 117; for moving the patient support along the elevator frame 118 in a support direction transverse to the pivot axis 119 and for tilting the elevator frame about axis 119 relative to the carriage. The actuator assembly may include any devices which can be used to impel mechanical elements relative to one another in a controllable manner.

The individual elements of the actuator assembly can be conventional elements as generally employed in automatic machinery. Those portions of the actuator assembly, carriage and patient support which extend within the patient-receiving space 67 during operation are desirably formed from non-magnetic materials and do not emit magnetic fields during operation. The carriage 116 is moveable on rails 117 extending into and out of magnetic frame through the patient entry openings 48 and 50.

Actuator assembly 122 is connected to a support controller 123, which in turn is connected to system controller 126. The support controller is connected to the control and feedback elements of the actuator. As further discussed below, the support controller is arranged to receive a command directing the support controller to bring the patient support to a first position, and to respond to such command by operating the actuator assembly 122 to drive the carriage relative to rails 117 and/or to move patient support relative to support frame 118 and/or to pivot the support frame about axis 119 relative to the carriage 116, until the feedback elements of the actuator assembly indicate that the patient support is in the first position, and to repeat these operations in response to a further command to bring the patient support to one or more different selected positions. The support controller may include conventional control elements capable of controlling fixed sequences of operations as, for example, conventional "hard-wired" electrical control apparatus, fluidic, mechanical or electromechanical control devices. Preferably, however, the support controller includes a general-purpose computer with conventional interface devices. For example, where the motion sources included in the actuator include electrical stepper motors, the support controller includes conventional stepper motor interface elements capable of providing electrical power to the stepper motors in response to commands from the processor in the computer. The interface devices in the support controller desirably also include conventional interfaces for receiving signals from the feedback devices in the actuator assembly. The support controller is depicted in FIG. 1 as a structure separate from the control and reconstruction computer 126 but operatively connected to the control and reconstruction computer. In this case, the support controller 123 and the system controller 126 desirably also includes interfaces permitting communication between these two controllers. Alternatively, the support controller 123 may be an integral part of the system controller 126. For example, the processor of the system computer may perform the logic functions of the system controller. In either case, the support controller 123 desirably also has direct connections to at least some of the input devices 103 as, for example, to a deadman's switch as mentioned above, so that the operator can manually interrupt any movement of the patient support in an emergency. Alternatively or additionally, some of the input devices 103 may be directly connected to elements of the actuator 122. For example, a deadman's switch can be arranged to interrupt power to the actuator so as to stop movement of the patient support in an emergency regardless of any action taken by the support controller 123.

A set of gradient coils 106 is physically mounted within the magnet frame. The gradient coils are arranged in a conventional manner to apply magnetic field gradients within the patient-receiving space. The gradient coils in turn are connected to a gradient coil driver 107 which is controlled by computer 126. In the conventional manner, the computer 126 can control the gradient coil driver to apply appropriate currents to the various gradient coils so as to provide magnetic field gradients in the desired direction within patient-receiving space 67 and to vary these gradients with time.

A conventional RF antenna 108 and RF transmitting and receiving apparatus 109 are also associated with the control and reconstruction computer 126. The antenna may include one or more elements positioned in the conventional manner within the magnetic frame, on the patient support 120 or even carried by the patient. The transmitting and receiving apparatus can be actuated by the computer to apply RF excitation signals and to receive the magnetic resonance signals emitted by the patient. The apparatus may use the same or different antenna elements for transmitting and receiving.

The apparatus further includes a system controller, also referred to as a control and reconstruction computer 126, linked to a display 101 such as a CRT or LCD display or printer and input/output devices 103 for entry of data and control commands into the computer. The control and reconstruction computer includes the conventional elements of a general-purpose computer, including a programmable processor and conventional memory devices, e.g., RAM and ROM, for storing data and programs. The memory stores information accessible by the processor, including instructions that may be executed by the processor and data that may be retrieved, manipulated or stored by the processor. The memory may be of any type capable of storing information accessible by the processor, such as a hard-drive, memory card, ROM, RAM, DVD, CD-ROM, write-capable, read-only memories. The memory may contain machine executable instructions or other software programs that embody the algorithms and methods described below.

The processor may comprise any number of well known processors, such as processors from Intel Corporation or AMD. Alternatively, the processor may be a dedicated controller such as an ASIC or a RISC processor.

The instructions may comprise any set of instructions to be executed directly (such as machine code) or indirectly (such as scripts) by the processor. In that regard, the terms "instructions," "steps," and "programs" may be used interchangeably herein. The instructions may be stored in object code form for direct processing by the processor, or in any other computer language including scripts or collections of independent source code modules that are interpreted on demand or compiled in advance. The functions, methods and routines of instructions in accordance with the present invention are explained in more detail below.

The data may be retrieved, stored or modified by the processor in accordance with the instructions that implement the processes or methods of the present invention. The data may be stored as a collection of data and will typically comprise the pixel data discussed above. For instance, although the invention is not limited by any particular data structure, the data may be stored in computer registers, in a relational database as a table having a plurality of different fields and records, XML documents, or flat files. The data may also be formatted in any computer readable format such as, but not limited to, binary values, ASCII or EBCDIC (Extended Binary-Coded Decimal Interchange Code). Moreover, the data may comprise any information sufficient to identify the relevant information, such as descriptive text, proprietary codes, pointers, references to data stored in other memories (including other network locations) or information which is used by a function to calculate the relevant data.

Although the processor and memory are functionally illustrated in FIG. 1 within the same block 126, it will be understood by those of ordinary skill in the art that the processor and memory may actually comprise multiple processors and memories that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

The input/output device 103 may include conventional elements such as a keyboard, as well as conventional pointing devices such as a mouse, touchpad or trackball, and preferably also include specialized command entry devices such as switches or pushbuttons used to control at least some aspects of the patient movement or imaging plane manipulation as discussed below. Computer 126 may comprise a desktop or laptop personal computer operating using a Windows or Apple (e.g., MAC) operating system. It may also comprise a workstation such as those offered by Sun Microsystems, Hewlett Packard, IBM or any other similar workstation.

Figure 2:
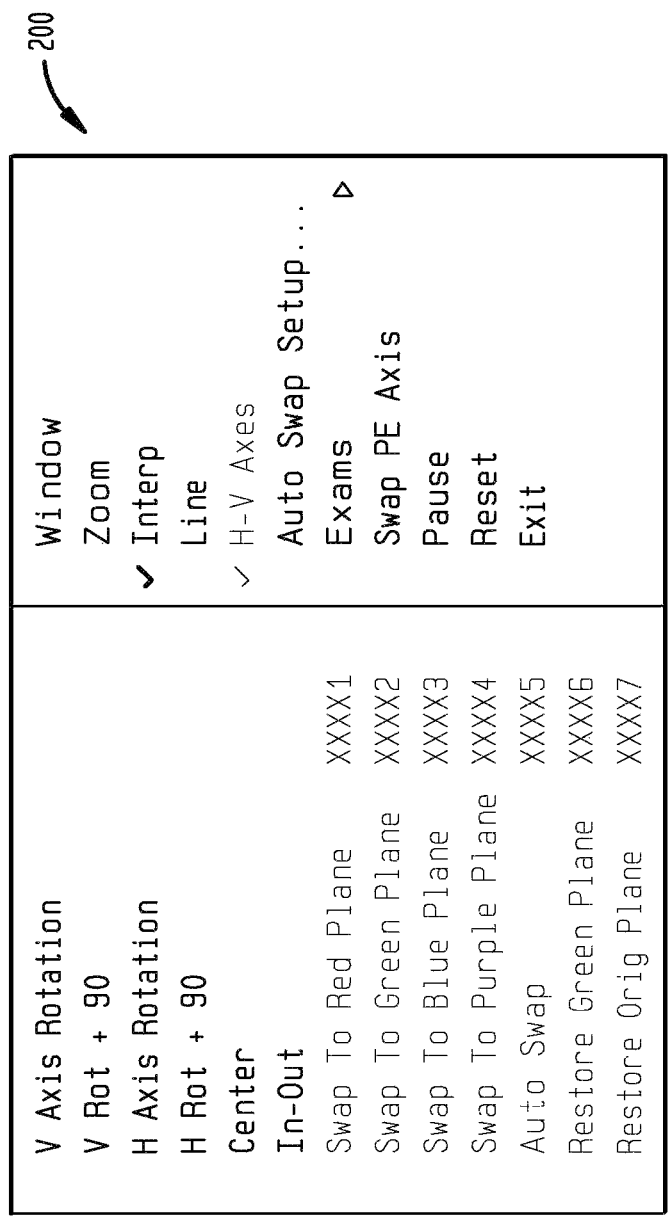
FIG. 2 shows a screen shot of menu functions used in accordance with an aspect of the present invention.

In accordance with an aspect of the present invention, computer 126 preferably includes an algorithm or process that is executed as machine instructions to allow for motion picture MRI. In that regard, the menu selections 200 shown in FIG. 2 are preferably included among those used. In one embodiment of the system the functions shown in menu 200 are selectable by clicking on one of the mouse buttons (e.g., the middle button or tracking wheel) thereby making the menu selections appear on the display 101 to the user. In other words, the menu 200 functions as a pop-up menu. However, other means may be provided to allow selection of these functions including selecting function keys on a keyboard or on a touch sensitive display.

The system is arranged to acquire two-dimensional sets of image data in a region of any arbitrarily-selected imaging plane. The region of the imaging plane included in the image data is referred to herein as the "slice." Of course, the slice must be disposed inside the imaging volume R (FIG. 1) of patient-receiving space 67 where the system is physically capable of acquiring an acceptable image. The system can specify the disposition of the imaging plane and slice in any convenient coordinate system. In one such coordinate system, the disposition of the imaging plane and slice are defined in the frame of reference or coordinate system of the physical magnet, indicated by mutually perpendicular axes X, Y, and Z in FIG. 3A. In this coordinate system the intersection of the X, Y, and Z axes (the zero point of the coordinate system) lies at the center of the imaging volume of the magnet. The imaging plane or plane of the slice is the plane including mutually perpendicular Z' and Y' axes, whereas the direction perpendicular to the plane is the X' axis. By default, the intersection of the X', Y', and Z' axes lies at the center of the slice unless an offset in the X', Y', or Z' direction is specified. The transformation between the X, Y, Z machine coordinate system and the X', Y', Z' coordinate system, and hence the disposition of the imaging plane, is defined by the length L of the vector in the X' direction, normal to the imaging plane connecting the zero point of the X, Y, Z coordinate system with the center point of the slice or zero point of the X', Y', Z' coordinate system, by the Euler angles $\theta$, and $\phi$ specifying the orientation of this vector relative to the X, Y, and Z axes, and by the further Euler angle $\Psi$ specifying the rotational position of the Z' axis about the normal vector or X' axis. The slice is further defined by one or more scale factors denoting the size of the slice, i.e., the size of the region in the Z', Y' plane from which data is acquired. The Z' axis is regarded as the vertical axis of the slice, whereas the Y' axis is regarded as the horizontal axis of the slice. Thus, when the image a slice is displayed, the Z' axis forms the vertical axis of the displayed image and the Y' axis is the horizontal axis of the displayed image. The system incorporates conventional features which allow the user to select one or more slices in arbitrary planes and acquire images of the selected slices. However, the system also incorporates additional functions referred to herein as a "RPM" or Rapid Plane Manipulation routine in which the system performs the functions associated with menu 200 (FIG. 2). Typically, the user actuates the system to acquire an image of a slice in a first imaging plane prior to entering the RPM, and that image is displayed and used as the "current" image in the RPM functions discussed below.

Most of the RPM functions selectable via the menu 200 allow the operator to specify the disposition of one or more additional slices which provide facile placement of the additional slices and easy visualization by the physician.

In particular, V Axis Rotation provides rotation of the current imaging plane about the vertical axis of the slice in the currently displayed image, i.e., rotation of the imaging plane about the Z' axis of the current imaging plane so as to define a new imaging plane. The rotation is continuous and preferably controlled by up-down mouse movements. Control may also be provided via keys on a keypad or via any other input device as discussed above. This mode is preferably exited with a right mouse button click.

V Rot+90 provides rotation of the current imaging plane in discrete 90 degree increments about the Z' axis of the current imaging plane so as to define a new imaging plane. Such rotations are controlled by left mouse button clicks. This mode is also preferably exited with a right mouse button click.

H Axis Rotation—Defines a new imaging plane by rotation of the current imaging plane about the Y' axis, i.e., about a line in space corresponding to a horizontal line through the center of the currently displayed image. The rotation is continuous and controlled by up-down mouse movements. This mode is preferably exited with a right mouse button click.

H Rot+90—same as H Axis Rotation, but uses discrete 90 degree increments. This action is controlled by left mouse button clicks. This mode is preferably exited with a right mouse button click.

Center—Re-centering (in-plane or Z'-Y' translation) of the imaging plane at the cursor position determined by a left mouse button click. Stated another way, if a slice has been acquired in the current imaging plane and the image of this slice is displayed on the display screen, each position in the displayed image corresponds to a position in the Z'-Y' plane. By bringing the cursor to a particular position in the displayed image, the user specifies a position in the Z'-Y' plane, and thus specifies a new position in the X, Y, Z frame of reference of the imaging system. The Center function shifts the zero point of the X', Y', Z' system to this new position but leaves the orientation of the imaging plane the same. If a further slice is acquired after execution of the Center function, it is centered at this new zero point.

In-Out—Translation of the imaging plane in the direction perpendicular to the current imaging plane, i.e., translation along the X' axis of the current imaging plane. The translation is continuous and controlled by up-down mouse movements. Exit this mode with a right mouse button click.

Line—The Line function, as well as the Swap functions discussed below, are operable after an image of a slice in a first imaging plane has been acquired. The term "original" image is also used to refer to this image. When the Line function is actuated, the system displays the original image with a first, green-colored line 202 (FIG. 3B) and a second, red-colored line 204 perpendicular to the first or green line overlaid on the original image. In the particular example of FIG. 3B, the original image is a saggital cut. The second or red line intersects the first or green line at one end of the first or green line and at the center of the second or red line. The user can manipulate the green line by placing the cursor on an end of the green line, holding down the left mouse button and dragging the end of the green line to an appropriate location on the displayed original image. In this manner, the user can change the orientation and length of the green line 202. During this process, the red line 204 remains perpendicular to the green line 202 and remains in position relative to the green line. The system keeps track of the positions of the first (green) and second (red) lines. The system interprets the first or green line as denoting a slice in a second imaging plane perpendicular to the first or original imaging plane, and interprets the second or red line as denoting a slice in a third imaging plane perpendicular to the first and second imaging planes. Stated another way, the displayed green and red lines constitute edge views of the slices in the second and third imaging planes. The "Swap" options discussed below can only be selected after the red and green lines have been placed using the Line option.

Swap To Red Plane—When the operator selects the "Swap to Red Plane" option, the system acquires an image of the slice in the third imaging plane discussed above in connection with the "Line" option, and displays this acquired image. The center of the slice is located at the position in space corresponding to the position of the intersecting red and green lines overlaid on the original image as discussed above. When the image of the slice in the red or third imaging plane is displayed, a red bulls eye 206 (FIG. 3C) will appear in the center of the image. The red bulls eye corresponds to an end view of the green line, i.e., an end view of the line of intersection of the first (original) and second (green) imaging planes. Stated another way, the red bulls eye 206 is an indicium denoting the end view of the line of intersection.

Swap To Green Plane—When the operator selects the "Swap to Green Plane" option, the system acquires an image of the slice in the second imaging plane discussed above in connection with the "Line" option, and displays this acquired image as seen in FIG. 3D. In the particular example shown, the green plane image is an axial image. The center of the slice is located at the position in space corresponding to the position of the center of the green line overlaid on the original image as discussed above. When the image of the slice in the second imaging plane is displayed, a horizontal dashed blue line 208 and a vertical dashed purple line 210, intersecting at the image center, will appear. The purple line 210, also referred to herein as the third line, denotes an edge view of a slice in the original or first imaging plane, which may or may not be in the same orientation as the original image. The blue line 208, also referred to herein as the fourth line, denotes an edge view of a slice in a fourth imaging plane parallel to the third imaging plane denoted by the red line discussed above.

Swap To Blue Plane—Actuates the system to acquire and display an image of a slice in the imaging plane denoted by the fourth or blue line 208. The blue plane image (FIG. 3E) is a coronal image. The center of the slice corresponds to the position of the center of the blue line shown during display of the green or second-plane slice. 'Swap To Green Plane' must be chosen first to activate this menu item.

Swap To Purple Plane—Actuates the system to acquire and display an image of a slice in the imaging plane denoted by the third or purple line 210, i.e., in the first or original imaging plane. In this example, the purple plane image is a saggital image (FIG. 3F). The center of the slice corresponds to the position of the center of the purple line shown during display of the green or second-plane slice. 'Swap To Green Plane' must be chosen first to activate this menu item.

Auto Swap—Actuates automatic swapping of the imaging plane between the green plane and either the blue (fourth) or purple (original) imaging plane. If the Swap to Purple Plane command was the last command used before actuation of the Auto Swap command, the system repeatedly acquires and displays images of slices in the second or green imaging plane and in the original or purple plane in alternating sequence. If the Swap to Blue plane item was used last, the system repeatedly acquires and displays images of slices in the second or green imaging plane and in the fourth or blue plane in alternating sequence. The swap period is determined by the settings chosen in the 'Auto Swap Setup' dialog box. The sequence of images need not be a 1-to-1 alternating sequence; the number of images in each plane acquired and displayed before changing over to the other plane used in the sequence can also be set using the Auto Swap Setup dialog box.

Restore Green Plane—The imaging plane is returned to the orientation of the green plane. Thus, the system acquires a new image of the same slice imaged in the Swap to Green Plane operation.

Restore Orig Plane—The system acquires and displays a new image of the same slice constituting the original image.

Window—Modification of the brightness and contrast of the currently displayed image. Brightness is controlled by left-right mouse movements and contrast is controlled by up-down mouse movements. Exit this mode with a right mouse button click.

Zoom—Modification of the magnification and pan settings of the displayed image. The magnification factor is controlled by holding down the left mouse button followed by up-down mouse movement. Up movement increases magnification while down movement decreases it. Releasing the left mouse button enters pan mode which is controlled by up-down and left-right mouse movement. Exit this mode with a right mouse button click. Note that this command does not change any of the imaging parameters such as the size of the slice (field-of-view) or the disposition of the slice. It however changes the appearance of the displayed image.

Interp—Toggles the interpolation of the displayed image on and off. With 'Interp' off, the image is displayed in its native resolution and may appear pixilated.

H-V axes—Toggles the blue and purple dashed lines on and off.

Auto Swap Setup—Invokes the dialog box used to control the number of green and blue/purple frames displayed when in 'Auto Swap' mode.

Exams—Invokes a drop-down menu with a selection of alternate exams. These exams may have differing scan parameters yielding different SNR, resolution, T1/T2 contrast, scan time, etc.

Swap PE Axis—Toggles the direction of the phase encode axis between the vertical and horizontal directions of the slice, i.e., between the Y' and Z' axes of the imaging plane.

Pause—Pauses the acquisition and display of image data until an exam is chosen from the 'Exams' drop-down menu.

Reset—Restores the gradient angles and x-y-z translations to the original values of the session start.

Exit—Exits the RPM (Rapid Plane Manipulation) screen and returns to the normal IDS screen.

The RPM routines discussed above allow the user to acquire images of any portion of the anatomy in mutually-perpendicular planes which facilitate three-dimensional visualization. For example, if the Z'-Y' plane or imaging plane of the original image is a sagittal cut as shown in FIG. 3B, then the second or green plane image (FIG. 3D) extends parallel to the X'-Y' plane of the original image and, in this case, is an axial cut. As is also shown, the red or third imaging plane (FIG. 3C) is parallel to the X'-Z' plane of the original image, and hence is a generally coronal plane. In the particular example of FIG. 3C, the red or third imaging plane, however, is not located within the anatomy of the patient. Rather, in this example, it is shown outside such anatomy and thus the image does not depict any of the anatomy. As explained below, such an imaging plane can be used in a procedure for guiding an instrument. As explained above, different planes are preferably shown as lines in the plane currently being viewed. Accordingly, as planes are swapped the user's perspective changes as does the lines that illustrate different planar views. The various commands can be used in sequence. For example, after a Swap to Red Plane command is input, and the system acquires a slice in the red or third imaging plane. This image becomes the current image. If an In/Out command is input at this stage of the operation, the system selects a new imaging plane parallel to the third imaging plane but offset from the third imaging plane in the direction normal to the third imaging plane, i.e., in the direction corresponding to the direction of the green line shown on the original image.

The foregoing description of the colored lines and planes is merely illustrative. As one skilled in the art may appreciate, the colored planes may be referred to using any other mnemonic. In addition, these planes may be arranged to be located along any of the axial, coronal, and sagittal slices, or any oblique plane. Therefore, the foregoing description is illustrative of the functions provided by this aspect of the present invention and is not meant to limit the present invention in any way.

The RPM procedures can be used in a method of placing an instrument such as a needle into the body of a subject. For example, the instrument may be a needle 212 (FIG. 3G) having an elongated structure with a distal end or tip 214 adapted for insertion into the body of the subject and with an MRI-visible locating element 216 mounted to the elongated structure remote from the distal end or tip. For example, the MRI-visible locating element may be a ring filled with an oil or other substance which has magnetic resonance properties distinct from those of typical body tissues so that the ring is readily seen in an MRI image. Desirably, the remainder of the structure, and particularly a portion of the structure at or near the tip, is also MRI-visible. For example, where the elongated structure includes a needle formed from a non-magnetic metal such as magnesium, the needle will be visible as a region devoid of magnetic resonance signals.

Initially, a conventional scan is run to capture parallel slices of the subject to locate the target anatomy or region of interest as, for example, a lesion within the body of the patient. Next, a multiplanar scan including slices in different planes containing the target anatomy is run. An MRI-visible marker such as vitamin E capsule is applied to the desired entry point on the anatomy. Next, a rapid plane manipulation (RPM) scan is initiated or started. The RPM scan may start with one of the planes of the multiplanar scan. Using the various RPM commands, such as center, H Axis Rotation, V Axis rotation and In/Out, the operator actuates the system to select and image slices until the displayed image shows both the target anatomy and the marker for the desired entry point. For example, the image depicted in FIG. 3B shows both a depiction of the target anatomy or lesion 218' and a depiction of the marker or entry point 220'. Desirably, the operator uses RPM commands such as Center to center the slice, and hence the image, on the target anatomy. Once the operator is satisfied that the entry point (as marked by an MRI visible marker 220') and target anatomy are both visible, the "Line" menu item is selected, step 624, to display the green line 202 and red line 204. The operator moves one end of the green line so that it overlies the image of the target anatomy 218' and moves the opposite end of the green line until the green line extends through the image of the marker 220' and out of the patient's body. By positioning the green line, the operator positions a linear path for entry of the needle. By examining the image in the original plane, with the green line superposed, the operator can ascertain that the green line, and hence the entry path, are clear of critical structures which the path must avoid. For example, green line 202 avoids the images 222' of structures which must be avoided as seen in the original image (FIG. 3B). By positioning the end of the green line, the operator also positions the red line 204, outside of the image of the patient's anatomy and hence positions the third imaging plane or red plane outside of the anatomy.

If the operator inputs a Swap to Green Plane command, the second-plane or green image (FIG. 3D) is acquired and shown. Because the purple or third line 210 shows the first plane of the original image in edge view, and the linear path defined by the green line lies in the first or original imaging plane, the path as seen in the green or second plane image (FIG. 3D) is coincident with the purple line. The physician can confirm that the purple line avoids the images 224' of critical structures, and thus confirm that the path avoids these structures.

The operator may return to the original plane and execute a Swap to Red Plane command. At this stage, the operator may position instrument 212 (FIG. 3F) so that the tip is aligned with the entry point. This positioning step may be performed manually or robotically. The operator may move the proximal end of the instrument to align the axis of the instrument with the path. The MRI-visible locating element 216 is disposed outside of the anatomy, in the imaging plane of the red or third-plane image (FIG. 3C). By aligning the marker with the bullseye 216, the operator may align the elongated instrument with the path. If the marker 216 is not visible, the operator may bring it into view by moving the imaging plane of the red or third-plane image along the path, as by executing In/Out commands while the red plane image is displayed.

Once the needle is aligned, the needle may be advanced to the target anatomy with uninterrupted tracking by the MRI system along the path denoted by the green line In addition, as the needle advances, the plane of view may be switched between the various imaging planes, either manually using the various swap commands, or in an automated sequence using the Auto Swap command as discussed above. In this manner, the needle can be tracked along the intended path in multiple, mutually orthogonal planes so that the operator can confirm that the advancing instrument is on the path, determine its depth of insertion and determine when the tip 214 has reached the target anatomy. The ability to see the instrument from multiple perspectives without complex manipulation of the MRI system controls, and the ability to see the intended path in at least one of these views, makes accurate placement of the instrument easier. Although the particular example of instrument navigation discussed above involves placement of a needle, the same navigation it may be used in any medical procedure where alignment of an object such as an instrument and a target anatomy are important. Other such applications include alignment of screws and other devices in orthopedic procedures such as hip replacement.

In a variant of the RPM functions discussed above, the various planes need not always be mutually perpendicular. For example, the RPM functions can be varied to provide two or more planes perpendicular to the original imaging plane but oblique to one another. Also, the functions can be varied to allow positioning of the planes independent of one another as, for example, positioning of the red line discussed above independent of the position of the green line.

The rapid plane manipulation or RPM functions described above can be used as part of a high level process shown in FIG. 4A that allows for changing the plane of an imaging slice along six degrees of freedom. This advantageously allows for manipulation of the imaging plane by a user while imaging data is being acquired and a scan is in progress such that the images may show changes in physiology of the anatomical area or region of interest so as to assess the functional capability of that region. Such changes in physiology may be caused, for example, by movement of a joint, breathing, flexion and extension, movement from a recumbent to upright position, etc.

As shown in FIG. 4A, the process begins when a user or operator initiates scanning or image acquisition, step 410. This results in the acquisition of imaging data for a particular anatomical region of interest. More specifically, this step usually requires the substeps of running a multi-planar scan centered on the anatomical region of interest to obtain one or more scout images and selecting a slice or plane from the scout image for scanning. This is generally referred to as acquiring of scout images. In the preferred embodiment, the user may choose to use a three plane scout scan. Using the scout image, the user then selects an imaging plane or slice through the anatomical area of interest that would then be used as part of the scanning process. That is, a scan would then be initiated using the imaging plane selected by the user. This results in the generation of particular pulse sequences, such as for example that which is described in commonly assigned U.S. Pat. No. 7,375,521, the disclosure of which is incorporated herein by reference, that generate gradient fields as described above. These gradient fields spatially encode magnetic resonance signals from the anatomical region of interest that are then used to construct the imaging plane or slice. In the conventional manner, the pulse sequence chosen determines the field of view, the resolution and other parameters relating to image acquisition.

With a slice selected and while image data acquisition is taking place, the user may adjust the imaging plane or slice, step 420, in the manner discussed above in relation to FIGS. 2 and 3. That is, the user may select a new location and orientation for the next imaging plane before data acquisition associated with the current pulse sequence is completed such that the next pulse sequence acquires an image at the newly selected imaging plane. Practical applications of this include moving the imaging plane along the x, y, or z axis, rotating it, or switching from a sagittal view of the region of interest to an axial, coronal, or any other view.

Once the next imaging plane is selected at step 420, the process then continues with a scan being performed at that imaging plane as is indicated at step 430.

In accordance with the foregoing steps, a user may move the imaging plane to track the functional capability of a particular portion of a patient's anatomy. For example, the plane may be moved (e.g., translated) along the vertebrae of the spine (e.g., L4 to L5) as the patient flexes from an upright position forward or vice versa. In addition, the imaging plane may be fixed on a particular vertebrae and rotated during such movement or switched from a sagittal to an axial view or vice versa. These are but a few possible applications of how rapid manipulation of the plane can be used to enable real time imaging of the physiology of the anatomical region of interest. In accordance with this aspect of the present invention, patient movement is not interrupted during imaging. Therefore, image data acquisition is not interrupted or stopped as the anatomy of interest changes location or position and/or undergoes a physiological change. Rather, the change in the anatomy or physiology of interest is captured in real time without interruption. Other applications of the present invention are discussed below.

As is also shown in FIG. 4A, in lieu of having the user change the imaging plane or slice, the process may operate by having the program or software on computer 126 automatically determine the next imaging plane based on movement of the patient as is described in block 440. For example, the movement of the patient may be controlled in conjunction with the selection of the next imaging plane. In one embodiment the movement of the user may be controlled by rotating the bed or patient support as, for example, by pivoting the elevator frame 118 (FIG. 1) and patient support 120 about pivot axis 119. In another embodiment the bed may be made such that it folds down thereby causing the patient to bend over. Stated another way, by moving a fixture such as the patient support 120 through a predetermined motion while maintaining the body part in contact with the fixture, the body part also moves through the predetermined motion. Accordingly, as the patient body part or anatomic region of interest containing a target region to be imaged moves, the pulse sequence can be adjusted based on the predetermined motion of the fixture such that the imaging plane moves along with the motion of the body part. Stated another way, a series of imaging planes is provided so that the imaging planes are correlated with the motion of the body part. Thus, at each stage of motion, the imaging plane includes the target region and is oriented in the same orientation relative to the target region. For example, where the target region is a particular spinal disc and the body part is the torso, the imaging planes used in successive stages of motion are correlated with motion of the torso so that the imaging planes remain in the same orientation relative to the disc. Merely by way of example, as described in U.S. Pat. No. 7,123,008, the disclosure of which is hereby incorporated by reference herein, data defining rotation of a patient support about a pivot axis can be used to calculate modifications of the gradients so as to maintain the imaging plane in the same orientation relative to the patient support and relative to the patient's body part engaged with such support. Such movement and fixtures may include that disclosed in the following commonly assigned U.S. Patent Applications, the disclosures of which are incorporated herein by reference: Ser. No. 10/987,822 (entitled "Planar Coil Flexion Fixture For Magnetic Resonance Imaging and Use Thereof,"; Ser. No. 10/304,582 (entitled "Method and Apparatus for Magnetic Resonance Imaging,"; and Ser. No. 10/694,963 (entitled "Transpolar Fixture,".

In a variant of this approach, the motion of the body part may be a voluntary movement by the patient or a movement manually impelled by an attendant. A tracking device may be maintained in contact with the body part during such motion, and the position of the tracking device may be monitored to provide data representing the movement of the body part. In similar manner, a non-contact tracking system such as a three axis pick-up coil, or optical tracking system, or other device associated with the movement may be used to provide data representing the movement. This data may be used to select a series of imaging planes correlated with the movement. In some instances, it may prove advantageous to acquire multiple scout images of the area of interest to accurately select an original imaging plane to be used as a basis for a series of imaging planes which are correlated with the movement of the body part.

Turning now to FIG. 4B, there is shown a method for motion picture MRI with auto tracking of the location of the anatomy of interest that is being imaged. In particular, the method 460 is described with respect to imaging a disk in the spine but may be also applied to any other region of the anatomy. The method begins at step 462 with the acquisition of a sagittal image. In this embodiment, the image acquired at step 462 would comprise a sagittal cut through the spine. At step 466, a decision is made whether to instantiate (i.e., start) the auto tracking feature. If auto tracking is selected, the process then continues to step 470 with local image enhancement. At step 470, image enhancement is used to facilitate detection of the particular disc, for example, that is the subject of the scan and whose movement will be automatically tracked. At step 474, feature extraction then takes place. In the process of doing object recognition, pixel patterns are analyzed and a set of features that can be matched to a template are determined. This enables identification of the object based on the features in the template. For example, identification of the object may be done via geometrical, intensity, or mathematical quantities (e.g., moments of inertia), etc. Such methods are known in the art.

After feature extraction 474, the process continues at step 480 with detection of the disc that is the subject of the scan. Once the disc is detected, its position and angle are computed at step 482. If the computation of the disc position and/or angle are satisfactory, the process then continues to step 486 with computation of a scout line, i.e., computation of an imaging plane which includes the disc and is oriented in the desired orientation relative to the disc. On the other hand, if the disc position and/or angle computation is unsatisfactory at step 482, the process returns to a position and/or angle predictor step 490 to enable better computation of the disc position and/or angle.

At step 486, scout line computation results in the position and angle of the disc or region of interest. That position and angle is then used at step 491 to acquire oblique axial images of the disc or region of interest. Once acquisition is completed at step 491, the process returns to step 462 and repeats. In this manner, as the body part (the patient's torso) moves, the system selects a series of imaging planes correlated with the movement. For example, as the patient's torso tilts, the newly-selected imaging planes will be in progressively tilted orientations. As is also shown in FIG. 4B, at step 466, the process may proceed with manual inputs from a user rather than use auto tracking. In the case where the user chooses to manually input the position and angle of the region of interest, that position and angle is then used to acquire oblique axial images of the disc.

FIG. 5 illustratively depicts possible movement of the axial plane 510 and 510' in relation to movement of a patient's spine 514, 514' as the patient bends forward 514' at an angle Q from an upright position 514. In the upright position the imaging planes 510 and 520 are used to provide coronal and axial views of the patient's spine, respectively. As the patient's body tilts or flexes forward, the coronal imaging plane 510' selected at a later stage is tilted forward with the spine. Although not shown for simplicity, the axial plane 520 will also tilt in correlation with the motion.

The images that are acquired in the manner described in FIGS. 4 and 5 may then be used to provide a moving picture or cine image of the target region by arranging the frames of images of the slices or imaging planes in time order and displaying these images in rapid sequence. Because the imaging planes used to acquire the images at the various stages of motion are correlated to motion of the body part, the target region remains substantially stationary in the cine image, and is viewed from the same viewpoint throughout the cine display. The changes in the target region caused by motion of the body part are depicted as progressive changes in the image. For example, in the case of a disc, the physician can see the disc bulge progressively with tilting movement of the torso. This cine display allows the physician to detect subtle changes which may not be readily visible simply by comparing still images taken at different positions of the body part.

In lieu of moving the imaging plane or slice with the region of anatomical interest, a three-dimensional image may be acquired such as by acquisition of volumetric three-dimensional data. In such an implementation, the imaging volume may remain fixed as the patient's anatomical region of interest moves through the volume. More specifically, three-dimensional acquisition of data, in accordance with this aspect of the present invention, enables display of multiple slices in any plane in a volume. For example, those planes may include a sagittal, coronal or axial plane. In addition, the slices may be located along different positions proximal to the region of interest, e.g., a plurality of sagittal images along the longitudinal axis of a patient. The three-dimensional imaging data that is acquired may then be used to construct a motion picture that depicts the movement of the anatomical area of interest through the volume along the planes. Furthermore, it is also possible to move the volume with the anatomical area of interest in a manner similar as described above with respect to moving a two-dimensional plane.

Other applications of the present invention also include motion picture imaging of the spine, which allow for example switching in real time between a sagittal and axial view of the region of interest, or switching between different vertebrae as the patient performs movement. Another application includes the tracking of a bolus or other substance as it moves through a patient's anatomy. For example, a motion picture MRI of the neck area of a patient drinking a substance (i.e., tracking movement of that portion of patient's anatomy during drinking) and neck movement (i.e., tracking cervical spine during movement) can be acquired.

In particular and turning now to FIG. 6, there is shown a process for acquiring motion picture MRI images during spinal or neck motion. The process begins by initially instructing a patient to assume a neutral sitting position, step 910. In addition to a sitting position, the patient may assume a standing position or any other position where motion of the spine is allowed. Next, at step 916, the appropriate rapid plane manipulation protocol is loaded in a controller. In this instance, the protocol comprises a method for cervical spine sagittal rapid plane manipulation. While the patient holds still, step 922, initial scout scans are performed until the desired mid-line cut is obtained, steps 928 and 934. Once the mid-line cut is obtained, a V-axis or H-axis rotation, step 940, is performed to modify the sagittal plane image until the desired oblique sagittal plane is obtained. In other words, the V-axis or H-axis rotation is performed to locate the particular imaging plane that will be used to acquire the motion picture sequence. In addition, the steps 934, 940 may be repeated as necessary until the region of interest is visualized as desired.

Next, the motion picture images are then acquired while the patient flexes and extends the spine through a full range of motion, step 946. In this regard, as flexion and extension motions are done, a rapid plane manipulation scan is initiated. As described above, the oblique sagittal plane may then be adjusted to track the motion of a particular disc in the cervical spine or more generally track with the movement of a larger section of the spine.

Moreover, as the scan is taking place, the pulse sequences may be changed to provide for higher resolution or different contrast, step 952. At step 958, the plane may be rotated as desired about the V-axis or H-axis, while the patient moves. In this regard, as the images are acquired, a motion picture is displayed on screen which shows not only the movement of the spine but also movement of the cerebral spinal fluid and may depict any constrictions in the flow of the fluid. Once the image acquisition process is completed, the rapid plane manipulation scan is exited, and the images acquired are displayed as a motion picture.

In addition to these applications, certain techniques discussed herein may also be applied as follows:

- Tracking movement of the joints, e.g., knee, wrist, ankle. For example, the present invention allows for motion picture MRI coronal imaging of the hand to aid in the diagnosis of carpal tunnel syndrome.
- Tracking movement of a bolus through the human anatomy, e.g., swallowing a capsule or water. In this regard, it is often important in stroke victims to monitor their ability to swallow liquids so as to know when to switch them from liquids to solid or, in the first instance, whether they can swallow at all. In general, this procedure may be used to perform an MRI GI series. For example, the movement of a bolus or other MRI visible substance (e.g., ice-cream) may track from entry in the mouth through the esophagus, stomach and upper and lower intestines.
- Cardiology motion picture
- Pulmonology motion picture
- Surgery motion picture
- Urinary tract motion picture, e.g., tracking the movement of urine along the urinary tract. In this regard, it may be necessary to mark the urine with an MRI visible substance. Furthermore, this application may allow for detection of prostate related maladies. For example, by tracking urine flow, the motion picture can show whether the urine flow is restricted by the prostate gland. In addition, it would visualize obstruction in the renal system due to stones.
- Defecography motion picture, i.e., tracking human bowel movement during the excretion process. In this regard, the magnet apparatus of FIG. 1 is uniquely suited since the patient can sit upright while imaging occurs. In contrast, longitudinal bore magnets do not allow for this procedure.
- Lyrangial motion picture, e.g., tracking movement of the vocal chords as they function during talking or singing.
- Medical device implantations, e.g., inserting one or more leads for a pacemaker at a particular location.

In view of the foregoing, certain techniques discussed herein provide means of assessing the physiology and functionality or functional integrity of an organ or portion of a patient's anatomy. In general, they provide tools to track the function of the human anatomy in different planes at the same time, e.g., sagittal and axial. These techniques allow tracking the functionality of different portions of the anatomy as they function, e.g., moving the imaging plane axially along different vertebrae of the spine or moving the imaging plane in and out of the anatomy.

In view of the foregoing, there are many aspects to the present invention. In one aspect, the present invention provides a method for performing motion picture magnetic resonance imaging comprising acquiring a first magnetic resonance image of a region of interest of a patient's anatomy at a first location defined by a first plane; determining a second location defined by a second plane associated with the region of interest of the patient's anatomy while the first magnetic resonance image is acquired; acquiring a second magnetic resonance image of the region of interest of the patient using the second location; and displaying the second magnetic resonance image and first magnetic resonance image in sequence such that they show a change in physiology associated with a change in position of the region of interest of the patient.

Further in accordance with this aspect of the present invention, the first plane may be associated with a sagittal cut of the patient's anatomy and the second plane may be associated with axial cut of the patient's anatomy.

Further in accordance with this aspect of the present invention, determining the second plane comprises receiving coordinate data from an input device. In addition, receiving coordinate data from an input device may comprise receiving coordinate data from an input device selected from the group consisting of a keyboard, mouse and track ball.

Further in accordance with this aspect of the present invention, receiving coordinate data from an input device may comprise receiving coordinate data from a fixture associated with controlled movement of the patient's anatomy.

Moreover, in accordance with this aspect of the present invention, receiving coordinate data from an input device may also comprise receiving location data associated with an MRI visible fiducial marker.

Yet further in accordance with this aspect of the present invention, the step of receiving coordinate data from an input device may comprise receiving location data from a processor.

Further in accordance with this aspect of the present invention, determining a second plane may comprise rotating the position of the first plane at an angle. In addition, rotating the position of the first plane may comprise changing an Euler angle associated with the first plane.

In accordance with this aspect of the present invention, determining the second plane may comprise selecting a plane that is orthogonal to the first plane. In addition, determining the second plane may comprise translating the position of the first plane along an axis perpendicular to the first plane.

Further still in accordance with the aspect of the present invention, displaying may comprise showing a change in physiology based on magnetic resonance images associated with movement of the region of interest and acquired during medical procedures selected from the group consisting of spinal imaging, joint imaging, urinary imaging, vocal cord imaging, bolus imaging, cardiology, pulmonology, defecography and surgery.

In accordance with another aspect of the present invention, a system for motion picture magnetic resonance imaging is provided. This system preferably comprises a magnetic resonance imaging magnet; and an apparatus coupled to the magnetic resonance imaging magnet and having a processor for receiving magnetic resonance imaging data acquired by the magnetic resonance imaging apparatus, the processor being associated with a memory having instructions that cause the processor to acquire first magnetic resonance imaging data associated with a region of interest of a patient anatomy at a first location defined by a first plane and determine a second location defined by a second plane associated with the region of interest of the patient anatomy while the first magnetic resonance image is acquired. In addition and in accordance with this aspect of the present invention, the processor may also acquire second magnetic resonance imaging data associated with a region of interest of that patient's anatomy using the second location.

Further in accordance with this aspect of the present invention, the magnet may be associated with a patient support that allows patients to be imaged in an upright position.

Further in accordance with this aspect of the present invention, the magnet may be associated with a patient's support that allows patients imaged in a recumbent position.

Further still in accordance with this aspect of the present invention, the magnet may also be associated with a patient support that allows the patient to be imaged in multiple positions from upright to recumbent.

Further in accordance with this aspect of the present invention, the system may also comprise a display coupled to the processor to display consecutively the first magnetic resonance imaging data and the second magnetic resonance imaging data as part of a motion picture magnetic resonance imaging movie.

Further in accordance with this aspect of the present invention, the second plane may be selected from the group consisting of a coronial, axial and sagittal plane. In addition, the first plane may be selected from the group consisting of a coronial, axial and sagittal plane.

In yet another aspect of the present invention, an apparatus is provided. The apparatus preferably comprises: a memory containing executable instructions; and a processor in communication with the memory and programmed to use the instructions to: acquire first magnetic resonance imaging data associated with a target anatomy of a patient and an imaging slice; acquire second magnetic resonance imaging data as the target anatomy moves relative to the imaging slice; and generate displayed data showing a functional change in the target anatomy based on the first and second image data as a motion picture.

Further in accordance with this aspect of the present invention, the processor may be programmed to continuously acquire image data associated with the imaging slice during uninterrupted motion associated with the target anatomy.

Further in accordance with this aspect of the present invention, the magnetic resonance imaging data may be acquired with the patient in an upright position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of magnetic resonance imaging comprising the steps of:
   (a) actuating a magnetic resonance imaging system to acquire an original image of a subject in a first plane by applying radio frequency energy to the subject and applying magnetic field gradients to the subject so as to elicit spatially-encoded magnetic resonance signals from the subject, the original image including at least one location of interest, and to display the original image in visually-perceptible form;
   (b) actuating the magnetic resonance imaging system to display first and second lines orthogonal to one another on the displayed image of the first plane so that the first line denotes an edge view of a second plane orthogonal to the first plane and the second line denotes an edge view of a third plane orthogonal to the first and second planes; and
   (c) responsive to input from an operator, actuating the magnetic resonance imaging system to acquire at least one image in at least one of the second and third planes by applying radio frequency energy to the subject and applying magnetic field gradients to the subject so as to elicit spatially-encoded magnetic resonance signals from the subject and to display the at least one image in visually-perceptible form,
   wherein step (b) includes actuating the imaging system to position and orient the second and third planes responsive to input from the operator and moving the first and second lines so as to represent moved positions of the second and third planes,
   wherein step (c) includes actuating the magnetic resonance imaging system to repeatedly acquire and display the images of at least two of said planes in alternating sequence in real time
   the method further comprising the step of providing a marker on the subject, wherein step (a) includes positioning the first plane at a location and orientation selected by input from the operator such that the image in the first plane includes a target region within the subject's body and the marker, and the step of actuating the imaging system to position the second plane responsive to input from an operator includes adjusting the position of the second plane so that the first line extends between the image of the target region and the image of the marker in the displayed image of the first plane.

2. A method as claimed in claim 1 wherein the step of moving the third plane includes adjusting the position of the third plane to a location outside of the subject's body.

3. A method as claimed in claim 1 further comprising the step of advancing an elongated instrument having a tip and having an MRI-visible locating element remote from the tip along a line of intersection between the first and second planes into the subject to the target region, while monitoring the displayed images.

4. A method as claimed in claim 3 wherein the step of moving the third plane includes adjusting the disposition of the third plane so that the third plane is disposed outside of the body of the subject but overlying the marker, and wherein step (c) includes displaying images of the first, second and third planes, the displayed images of third plane including an indicium denoting an end view of the line of intersection of the first and second planes.

5. A method as claimed in claim 4 wherein the third plane intersects the locating element of the instrument and the displayed images of the third plane include an image of the locating element of the instrument, the method further comprising the step of moving the instrument so as to align the image of the locating element with the indicium denoting the end view of the line of intersection.

6. A method as claimed in claim 3 further comprising the step of actuating the magnetic resonance imaging system to display third and fourth lines perpendicular to one another on the displayed image of the second plane so that the third line denotes an edge view of the first plane.

7. A method of magnetic resonance imaging comprising the steps of:
   (a) actuating a magnetic resonance imaging system to acquire an original image of a subject in a first plane by applying radio frequency energy to the subject and applying magnetic field gradients to the subject so as to elicit spatially-encoded magnetic resonance signals from the subject, the first plane being selected based on input from an operator so that the original image includes an image of a target region, and to display the original image in visually-perceptible form;
   (b) actuating the magnetic resonance imaging system to display a first line on the displayed image of the first plane so that the first line denotes an edge view of a second plane orthogonal to the first plane and adjusting the position of the second plane responsive to input from an operator so that the first line extends to the image of the target region, whereby a line of intersection between the first and second planes extends to the target region;

(c) actuating the magnetic resonance imaging system to repeatedly acquire images of at least of the first and second planes by applying radio frequency energy to the subject and applying magnetic field gradients to the subject so as to elicit spatially-encoded magnetic resonance signals from the subject and to repeatedly display the images of at least the first and second planes in visually-perceptible form; and, concurrently with the repeated acquisition and display, (d) confirming, based on the displayed images of the first and second planes, that the line of intersection avoids critical structures; and (e) advancing an elongated instrument to the target region along the line of intersection between the first and second planes, while monitoring the displayed images of at least the first and second planes.

8. A method as claimed in claim 7 further comprising the step of providing a marker on the subject, wherein the image in the first plane includes the target region within the subject's body and the marker, and the step of moving the second plane includes adjusting the position of the second plane so that the first line extends between the image of the target region and the image of the marker in the displayed image of the first plane, whereby the line of intersection between the first and second planes extends from the target region to the marker.

9. A method as claimed in claim 7 further comprising the steps of actuating the magnetic resonance imaging system to display a second line on the displayed image of the first plane so that the second line denotes an edge view of a third plane orthogonal to the first plane and non-coplanar with the second plane and adjusting the position of the third plane to a location outside of the subject's body, and wherein step (c) includes displaying images of the first, second and third planes, the displayed images of third plane including an indicium denoting an end view of a line of intersection of the first and second planes.

10. A method as claimed in claim 9 wherein the third plane intersects the locating element of the instrument and the displayed images of the third plane include an image of a locating element of the instrument, the method further comprising the step of moving the instrument so as to align the image of the locating element with the indicium denoting the end view of the line of intersection.

* * * * *